(12) United States Patent
Balakrishnan

(10) Patent No.: US 10,335,538 B2
(45) Date of Patent: Jul. 2, 2019

(54) SYSTEM AND TREATMENT METHOD TO INCREASE CIRCULATION AND PLURIPOTENCY OF STEM AND PROGENITOR CELLS WITHIN A PATIENT

(71) Applicant: Priya Visweswaran Balakrishnan, Houston, TX (US)

(72) Inventor: Priya Visweswaran Balakrishnan, Houston, TX (US)

( * ) Notice: Subject to any disclaimer, the term of this patent is extended or adjusted under 35 U.S.C. 154(b) by 326 days.

(21) Appl. No.: 15/413,410

(22) Filed: Jan. 23, 2017

(65) Prior Publication Data
US 2017/0157318 A1   Jun. 8, 2017

Related U.S. Application Data

(63) Continuation-in-part of application No. 15/373,453, filed on Dec. 8, 2016.

(60) Provisional application No. 62/281,616, filed on Jan. 21, 2016, provisional application No. 62/281,919, filed on Jan. 22, 2016, provisional application No. 62/264,522, filed on Dec. 8, 2015.

(51) Int. Cl.
| | |
|---|---|
| *A61M 5/00* | (2006.01) |
| *A61M 5/14* | (2006.01) |
| *A61K 33/00* | (2006.01) |
| *A61M 16/06* | (2006.01) |
| *A61M 5/145* | (2006.01) |
| *A61M 5/158* | (2006.01) |
| *A61M 5/168* | (2006.01) |
| *A61B 17/132* | (2006.01) |

(52) U.S. Cl.
CPC ......... *A61M 5/1407* (2013.01); *A61B 17/132* (2013.01); *A61K 33/00* (2013.01); *A61M 5/145* (2013.01); *A61M 5/158* (2013.01); *A61M 5/16831* (2013.01); *A61M 16/0666* (2013.01); *A61M 2005/006* (2013.01); *A61M 2005/16863* (2013.01); *A61M 2202/0208* (2013.01); *A61M 2202/0216* (2013.01)

(58) Field of Classification Search
CPC .............. A61M 5/3294; A61M 5/1407; A61M 2005/006
See application file for complete search history.

(56) References Cited

U.S. PATENT DOCUMENTS

| | | | | |
|---|---|---|---|---|
| 6,399,664 B2* | 6/2002 | Smith | .................... | A61K 31/08 424/45 |
| 2005/0281445 A1* | 12/2005 | Marcotte | .............. | A61B 5/0059 382/128 |

(Continued)

*Primary Examiner* — Bhisma Mehta
*Assistant Examiner* — Matthew A Engel

(57) ABSTRACT

A treatment method that increases circulation and pluripotency of stem and progenitor cells within a patient can be used to fight off or cure various diseases for the patient such as chronic kidney disease or end-stage renal disease. An administrator of the treatment method is provided with a medicinal-administration system such as an intravenous injection system. The treatment method begins by preparing a dosage of oxygen-ozone mixture with the medicinal-administration system. The medicinal-administration system then transfuses the oxygen-ozone mixture in the patient's bloodstream so that the renal system and/or the bone marrow can be targeted by the oxygen-ozone mixture. These steps are repeated as a plurality of treatment session for the patient.

23 Claims, 8 Drawing Sheets

(56) References Cited

U.S. PATENT DOCUMENTS

| | | | |
|---|---|---|---|
| 2012/0039796 A1* | 2/2012 | Markou | A61K 9/107 424/1.11 |
| 2016/0175353 A1* | 6/2016 | Caplan | A61K 33/40 424/93.7 |
| 2017/0157317 A1* | 6/2017 | Balakrishnan | A61M 5/1407 |
| 2017/0246375 A1* | 8/2017 | Spearman | A61M 1/369 |
| 2018/0133248 A1* | 5/2018 | Caplan | A61P 39/00 |
| 2018/0264132 A1* | 9/2018 | Michaeli | A61K 47/6873 |

* cited by examiner

SYSTEM AND TREATMENT METHOD TO INCREASE CIRCULATION AND PLURIPOTENCY OF STEM AND PROGENITOR CELLS WITHIN A PATIENT

The current application is a continuation-in-part (CIP) application of a U.S. non-provisional application Ser. No. 15/373,453 filed on Dec. 8, 2016. The U.S. non-provisional application Ser. No. 15/373,453 claims a priority to a U.S. provisional application Ser. No. 62/264,522 filed on Dec. 8, 2015.

The current application also claims a priority to a U.S. provisional application Ser. No. 62/281,616 filed on Jan. 21, 2016 and a priority to a U.S. provisional application Ser. No. 62/281,919 filed on Jan. 22, 2016. The current application is filed on Jan. 23, 2017 while Jan. 21, 2017 and Jan. 22, 2017 were on a weekend.

FIELD OF THE INVENTION

The present invention generally relates to treating a patient with an oxygen-ozone mixture. More specifically, the present invention is able to reverse kidney disease and other chronic medical conditions, by increasing circulation and pluripotency of stem and progenitor cells within the patient.

BACKGROUND OF THE INVENTION

A first objective of the present invention is to increase the following factors: circulating numbers of stem cells such as hematopoietic stem cells (HSC) and hematopoietic progenitor cells (HPC); circulation numbers of progenitor cells such as endothelial, renal, nephron, musculoskeletal, neuronal, and other progenitor cells; and precursor cells. A second objective of the present invention is to increases the pluripotency of those progenitor and stem cells that are capable of being pluripotent. Both the first objective and the second objective of the present invention can be achieved by a patent at any age and in any underlying state of health or disease, which includes, but is not limited to, chronic kidney disease (CKD), end-stage renal disease (ESRD), diabetes mellitus (DM), cerebro-vascular disease (CVD), coronary artery disease (CAD), neurological diseases, heart disease of any etiology, lung diseases, and aging. The present invention can also replace the need for bone marrow transplants in elderly patients or for other diseases that require an increased count of stem or progenitor cells, and rescue patients from chemotherapy induced bone marrow ablation and radiation therapy or toxicity induced myelo-ablation.

The present invention is thought to work by causing the multiplication of primitive mesoderm cells in their niche, and a release of the multiple stem cell, progenitor and precursor products of these and other stem cells, progenitor cells and precursor cells, which can give rise to bone, muscle, nerves, blood vessels, kidney and other tissues, into the circulating blood. In addition, the present invention also causes HSCs and HPCs to de-differentiate or differentiate into several organ-generating precursors (between primitive mesoderm and HSCs stage). Indications for its usage include, but are not limited to, several conditions: kidney failure (CKD for stages 1 through 5 and ESRD); stroke, multiple sclerosis, gout, diabetes, osteoarthritis, autoimmune diseases, every infectious disease and all degenerative diseases, and infectious diseases, inflammatory and autoimmune diseases.

A person who falls and breaks their bone at the age of 90, and then heals this bone back, is not an exception (a 1 in 1000 miracle) to the rule (which was previously thought, of, as standard order for 999/1000) of aging, disease and death. All 1000/1000 human beings are supposed to be able to do this, we postulate. Therefore, we state categorically, that if the Regenerative Organ System of people functioned the same way as it did in the healthy elderly, it is the norm, and it is the standard to which one aspires to. We must make happen and solidify our acceptance that the rule of normal health functionality is a high functioning Regenerative Organ System, and not make this normal functionality, the exception to the perceived rule of mandatory aging, illness, and death.

Hence, we postulate that there exists a Regenerative Organ System within the body. The kidney is the "brain" of this Regenerative Organ System, and the bone marrow is the "spinal cord" of the Regenerative Organ System. Dr. Arjun Raj of UPenn has described cellular members of the orchestra of this putative Regenerative Organ System, which he refers to, as immortal cells. That when all works well, the Regenerative Organ System should be able to revive a damaged organ, cell, or organ system, or the interconnection and inter-communication between these. We hypothesize that the communication between different elements of the Regenerative Organ System to trigger regeneration as is observed utilizing our protocol, is effected by the sensing of the oxygen molecules by neurons in blood vessel walls, which by becoming syncytial in nature, communicate instantly this message to end organs where stem and progenitor cells are made—such as, and most especially, the kidney, and the effector organ or executive arm of the regenerative organ system, namely, the bone marrow; and not just elements within the blood circulation, such as actual stem cells, or even, the amount of circulation.

There is an existent underlying network of neurons all over the body, that permit communication between the brain, spinal cord, nerves and all tubular systems including the genito-urinary system, the respiratory tract, the lympho-vascular system, the gastro-intestinal tract. It is when neurons in this intricate reticular (which means lace-like) network, fall out due to stress (patchy neuronal death), that we see disease depending upon where the neurons fall out—the diseases manifest, and when the amplitude of the current of life energy, through this reticular network of body-wide neurons, diminishes, then aging is caused. Usually, it is a combination of both, that results in death. This is our hypothesis, which is called the final common pathway of organismal aging, disease and demise (FCPOADD). The pathogenetic mechanism of the FCPOADD is patchy neuronal death. If every fifth neuron dies, or the life energy in the entire network diminishes to a fifth, aging results. If a group of neurons dies out in the pancreas, diabetes can result. If every fifth neuron dies out in the colon, for example, constipation might result. If a patch of neurons dies out in the colon, diverticulosis might result. The disease that manifests depends upon where the neurons die out, in a concentrated fashion or manner.

We believe that the Regenerative Organ System is capable of regenerating these neurons that have dropped out, by mechanisms no one has described previously. Also, the Regenerative Organ System seems to require the presence of Vitamin B12 for neuronal nutrition and Vitamin D for neuronal syncytium formation (in blood vessel walls and all over the body, to communicate the message of abundant availability of protective Vitamin B12 and oxygen-molecule combinations or oxygen gas alone, as is administered in our protocol, to hyper-drive oxidative phosphorylation or larger quantities of cellular energy synthesis, which uniformly facilitates cellular healing, by facilitating proper protein folding and proper enzymatic action, degradation and autophagy as and where indicated). It is also postulated that Vitamin B12 is required to mitigate the effects of cosmic radiation on the Regenerative Organ System, or any type of unwanted radiation on this. This can be proven by the destruction of hematopoietic stem cells and regenerative system, by Acute Radiation Syndrome caused by poisoning with nuclear isotopes such as Polonium 210, as was witnessed in the poisoning of agent Alexander Litvinenko. We believe that our protocol, by regenerating the Regenerative Organ System, will not only reverse chronic medical illnesses, it will also reverse radiation toxicity, and chemotherapy toxicity to the regenerative elements in the bone marrow and kidney, and even as they circulate and shut down the regenerative functionality within the kidney, and seek to patent this concept as well—that.

DETAILED DESCRIPTION OF THE INVENTION

All illustrations of the drawings are for the purpose of describing selected versions of the present invention and are not intended to limit the scope of the present invention.

General Overview of the Invention

Figure 1:
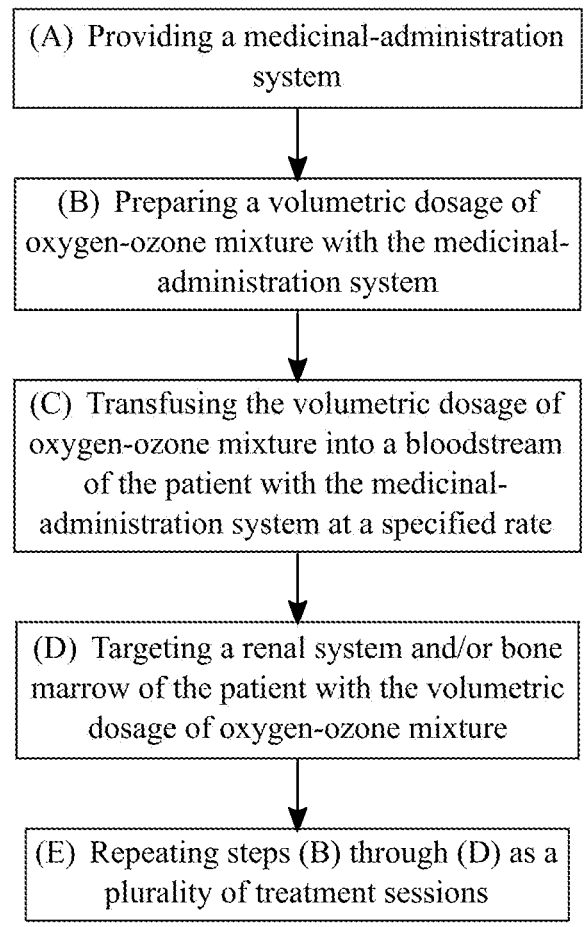
FIG. 1 is a flowchart illustrating an over process for the method of the present invention.

As can be seen in FIG. 1, the present invention is a system and a treatment method to increase circulation and pluripotency of stem and progenitor cells within a patient. The stem and progenitor cells provide the patient with certain internal regenerative abilities, and, thus, the increase of stem and progenitor cells allows the patient to fight off or cure various kinds of diseases. In order to complete the overall process of the present invention, an administrator for the present invention is provided with a medicinal-administration system (Step A), which can be, but is not limited to, medical equipment used for injections, medical equipment used for rectal insertion, and medical equipment used for dialysis. The administrator should also be a licensed medical practitioner.

The overall process of the present invention allows the administrator to treat the patient with an oxygen-ozone mixture. The overall process begins by preparing a volumetric dosage of oxygen-ozone mixture with the medicinal-administration system (Step B), which is used to retain the volumetric dosage of oxygen-ozone mixture, until this dosage is given to the patient. The volumetric dosage of oxygen-ozone mixture needs to accurately measure out by the administrator because too much or too little of the oxygen-ozone mixture can adversely affect the patient. In the preferred embodiment, the volumetric dosage of oxygen-ozone mixture is composed of 96% oxygen and 4% ozone. The overall process continues by transfusing the volumetric dosage of oxygen-ozone mixture into the bloodstream of the patient with the medicinal-administration system at a specified rate (Step C), which allows the health benefits of the oxygen-ozone mixture to take effect on the patient's body. The specified rate depends on the kind of medicinal-administration system that is used in the overall process. The overall process proceeds by targeting the renal system and/or bone marrow of the patient with the volumetric dosage of oxygen-ozone mixture (Step D). Creation of stem and progenitor cells occurs within the renal system (or more specifically, the kidneys) and the bone marrow. Consequently, the present invention can increase circulation and pluripotency of stem progenitor cells within the patient by stimulating the renal system and the bone marrow of the patient with the oxygen-ozone mixture. The overall process concludes by repeating Step B through D as a plurality of treatment sessions (Step E), which allows the health benefits of the oxygen-ozone mixture to compound onto the patient over a period of time. For the initial treatment session, the volumetric dosage of oxygen-ozone mixture during an initial session is approximately within a range of 5 to 20 milliliters (mL) and proportionately depends upon a weight and a habitus of the patient.

Figure 2:
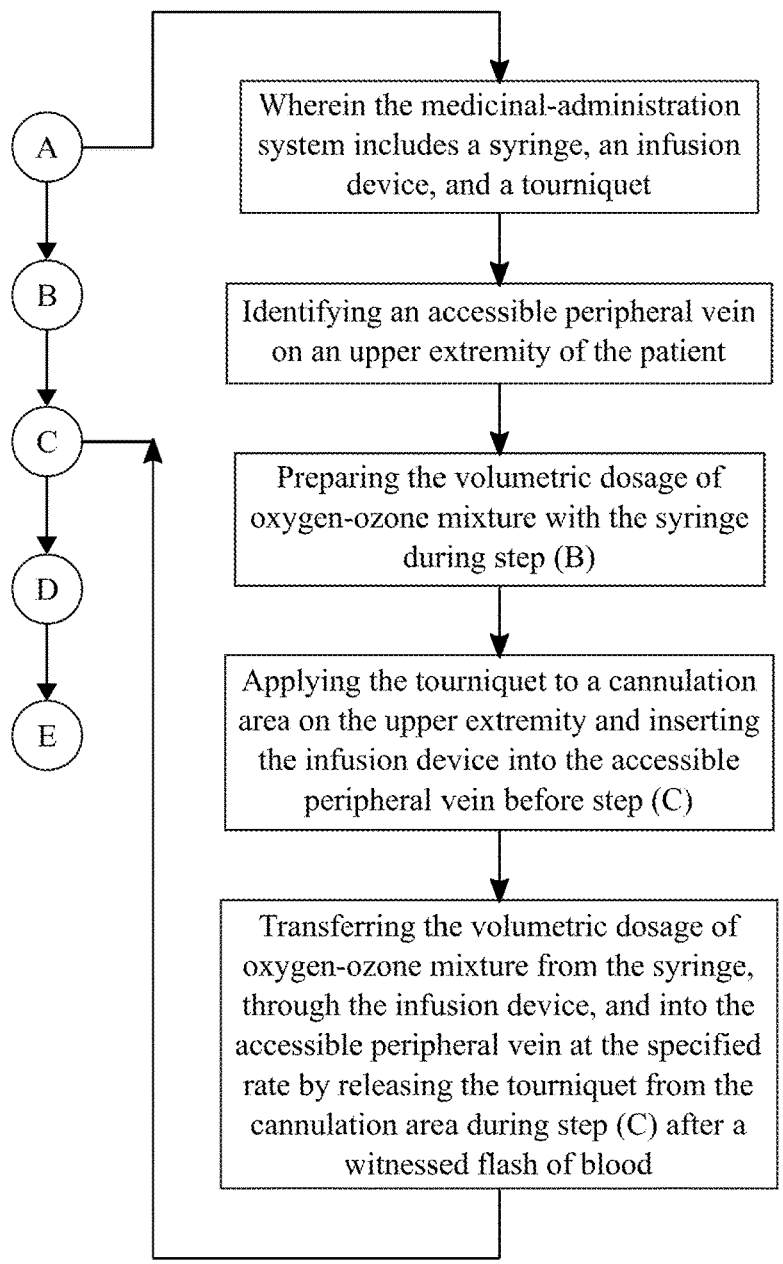
FIG. 2 is a flowchart illustrating a sub-process for implementing a specific embodiment of the medicinal-administration system.

In the preferred embodiment of the present invention shown in FIG. 2, the medicinal-administration system includes a syringe, an infusion device, and a tourniquet and requires the administrator to identify an accessible peripheral vein on an upper extremity of the patient. The upper extremity is preferably the arm or the elbow of patient. The administrator then prepares the syringe with the volumetric dosage of oxygen-ozone mixture during Step B. The syringe should be able to retain 50 to 60 mL. In addition, the administrator applies the tourniquet to a cannulation area on the upper extremity and subsequently inserts the infusion device into the accessible peripheral vein before Step C. The tourniquet is applied to the cannulation area in order to improve blood circulation through the veins of the patient, which in turn allows for easier execution of Step C. The infusion device is preferably configured into a 27-gauge winged setup and is in fluid communication with the syringe. After the administrator witnesses a flash of blood within the cannulation area, the administrator releases the tourniquet from the cannulation area. This consequently transfers the volumetric dosage of oxygen-ozone mixture from the syringe through the infusion device, and into the accessible peripheral vein at the specified rate during Step C. The volumetric dosage of oxygen-ozone mixture is able to enter the bloodstream of the patient through the accessible peripheral vein. In the preferred embodiment, the rate is approximately 1 mL every 30 to 60 seconds, and the preferred duration for Step C should last ten minutes. Yet, the proper infusion rate is proportionally dependent on the diametric size of the accessible peripheral vein. Thus, the administrator can adjust the specified rate to be proportionately slower if the accessible peripheral vein has a smaller diameter.

Figure 6:
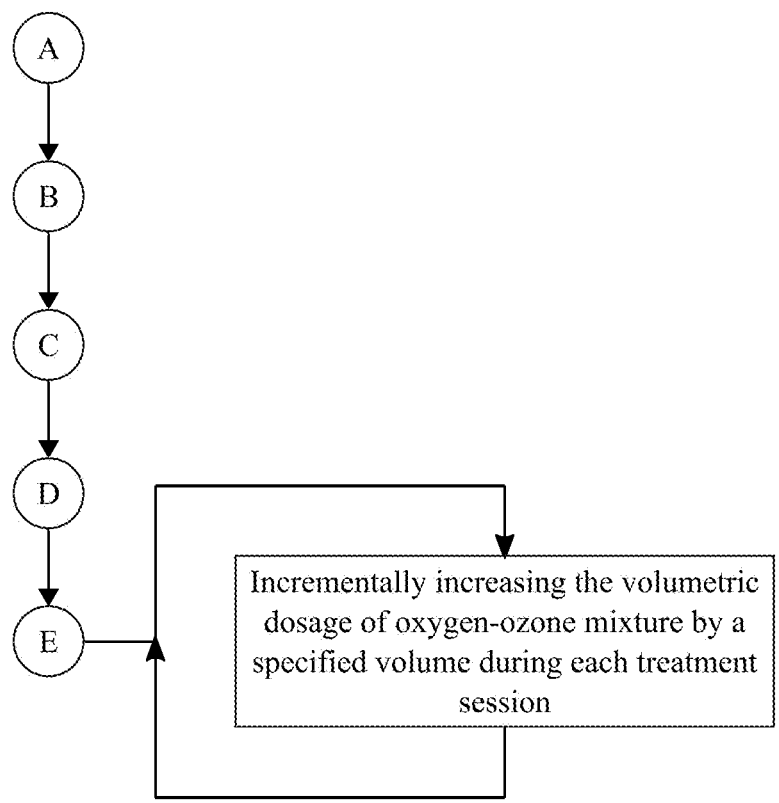
FIG. 6 is a flowchart illustrating a sub-process to more effectively execute the treatment sessions.

As can be seen in FIG. 6, the present invention also allows for the volumetric dosage of oxygen-ozone mixture to be increased by a specified volume during each treatment session, which allows the patient to garner the most health benefits from receiving multiple treatment sessions. The specified volume is a dosage escalation that is proportionately depended upon a weight, a habitus, and an underlying health condition of the patient. In the preferred embodiment, the volumetric dosage of oxygen-ozone mixture is increased within a range of 5 to 10 mL in each successive treatment session. However, the dosage escalation can be reduced or completely removed if the patient is experiencing procedural complications such as Herxheimer reaction, expresses discomfort, cough, chest tightness, facial flush, or vein irritation. Vein discomfort may be mitigated by slowing down the infusion rate. In addition, the administrator must also make sure to prevent any infiltration.

Typically, the present invention requires twenty treatment sessions in order for the patient to experience the full healing effects of the oxygen-ozone mixture. However, the administrator needs to supervise the patient's intake of the oxygen-ozone mixture through these twenty treatment sessions. The administrator should prevent the volumetric dosage of oxygen-ozone mixture for a tenth treatment session (or the halfway point) from exceeding 50 mL. The administrator should also prevent the volumetric dosage of oxygen-ozone mixture for a later treatment session from exceeding 110 mL, wherein the later treatment session occurs after the tenth treatment session.

Figure 3:
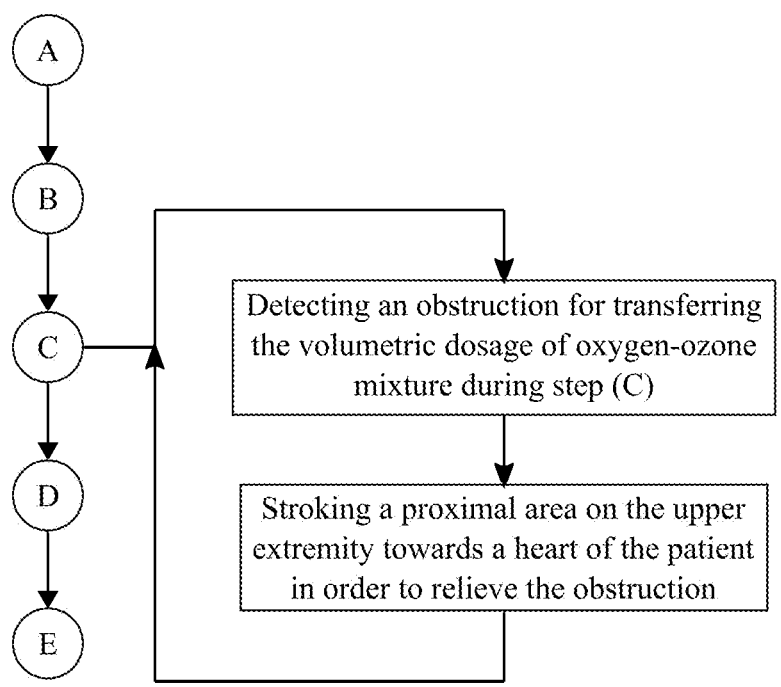
FIG. 3 is a flowchart illustrating a sub-process to more efficiently administer the intravenous oxygen-ozone mixture.
Figure 4:
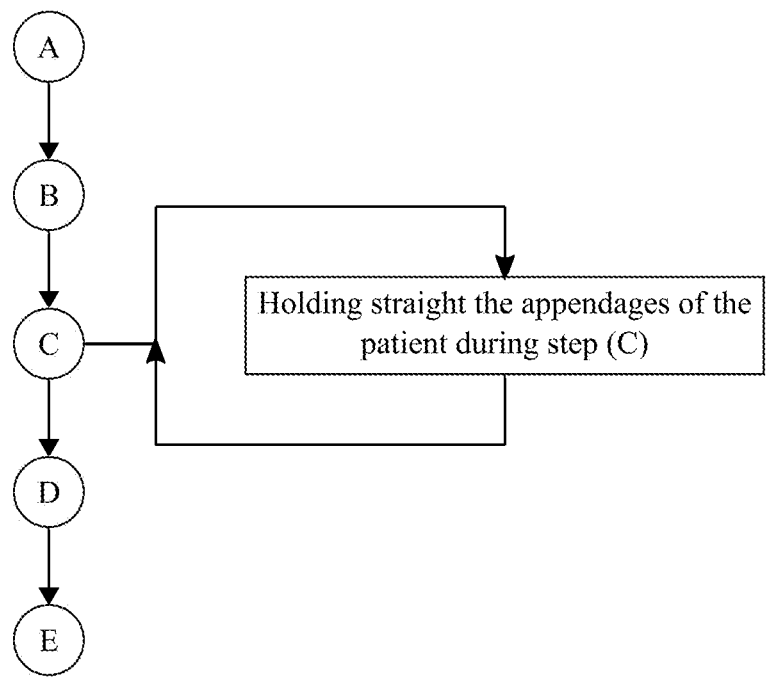
FIG. 4 is a flowchart illustrating another sub-process to more efficiently administer the intravenous oxygen-ozone mixture.
Figure 5:
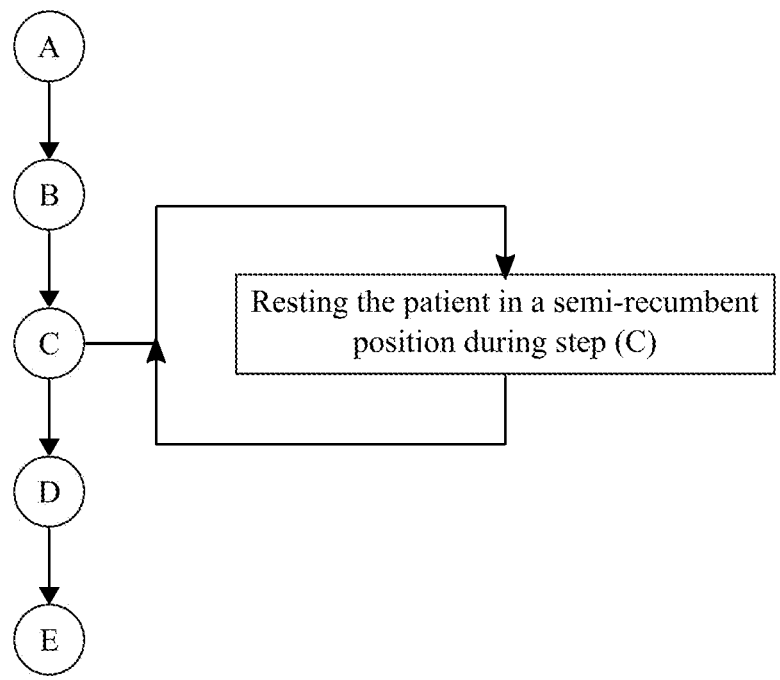
FIG. 5 is a flowchart illustrating another sub-process to more efficiently administer the intravenous oxygen-ozone mixture.

The present invention also allows for different actions to improve the efficiency of Step C. One such action is to reduce the specified rate during Step C when the patient is feeling pain or discomfort so that the oxygen-ozone mixture is more slowly transferred into the bloodstream of the patient. Another such method is provided the patient with oxygen through a nasal cannula when the patient is feeling pain or discomfort. The administrator should supervise the patient while the patient is receiving oxygen through the nasal cannula and until the patient is relieved of his/her pain or discomfort. Another such action can be implemented only when the syringe, the infusion device, and the tourniquet are being used as the medicinal-administration device. In reference to FIG. 3, the administrator or the patient need to detect an obstruction for transferring the volumetric dosage of oxygen-ozone mixture during Step C. In order to relieve or unblock the obstruction, the administrator can stroke the proximal area on the upper extremity towards the heart of the patient. This stroking or "milking" movement by the administrator should relieve the obstruction felt by the patient. In reference to FIG. 4, another such action is to have the patient straighten their appendages during Step C, which prevents an obstruction from occurring as the volumetric dosage of oxygen-ozone mixture transfers into the accessible peripheral vein. This means that the patient's appendages should be outstretched and not bent. In reference to FIG. 5, another such action is to have the patient resting in a semi-recumbent position in order to improve the efficiency of Step C. Another such action is to have the patient do a weight-lifting exercise to improve circulation around the cannulation area. Another such action is to have the patient drink plenty of liquids and be hydrated before a treatment session.

Figure 7:
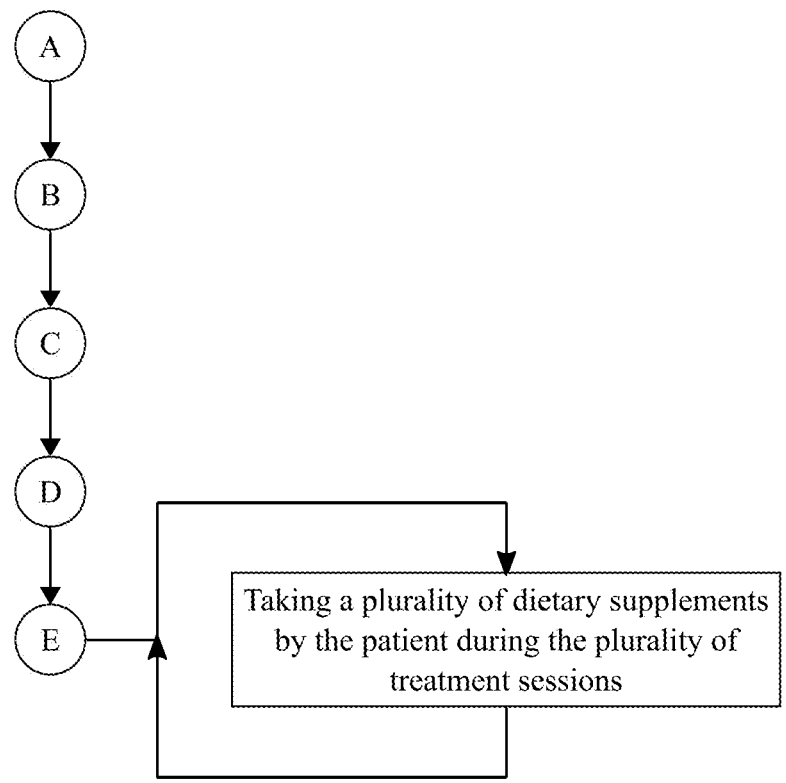
FIG. 7 is a flowchart illustrating another sub-process to more effectively execute the treatment sessions.

Moreover, the present invention provides the patient with a plurality of dietary supplements that can be concurrently taken as the patient is completing the plurality of treatment sessions for the oxygen-ozone mixture, which is shown in FIG. 7. The plurality of dietary supplements is used to assist the health benefits garnered from the oxygen-ozone mixture as the patient makes their recovery. The plurality of dietary supplements can include, but is not limited to, a daily dosage of Vitamin C, a daily dosage of Vitamin D, a daily dosage of Vitamin B12, a daily dosage of curcumin, a daily dosage of probiotic food and/or drink, and a daily dosage of water.

Figure 8:
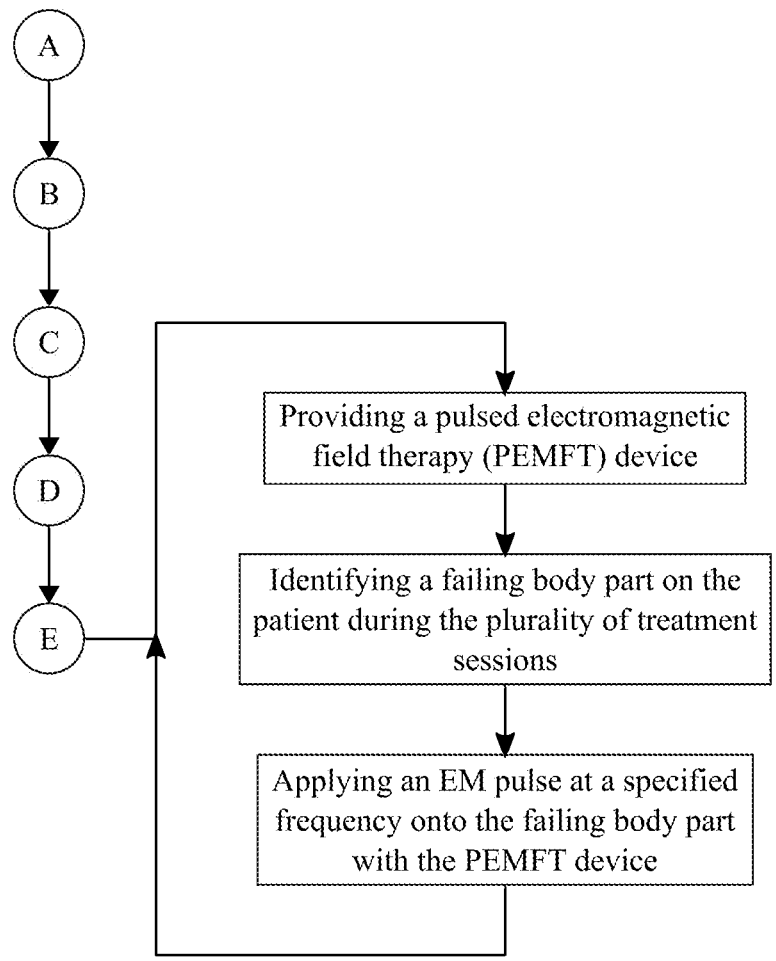
FIG. 8 is a flowchart illustrating another sub-process to more effectively execute the treatment sessions.

As can be seen in FIG. 8, the present invention also uses electromagnetism in order to supplement the plurality of treatment sessions and to assist in patient's recovery. The present invention is provided with a pulsed electromagnetic field therapy (PEMFT) device. The administrator considers using the PEMFT device if the patient has a failing body part that is not responding to the plurality of treatment sessions. Thus, the administrator must identify the failing body part and then apply an EM pulse at a specified frequency onto the failing body part with the PEMFT device, which allows the failing body part to receive additional treatment in conjunction with the oxygen-ozone mixture. In the preferred embodiment, the specified frequency of the EM pulse is 77 Hertz (Hz).

Specific Overview of the Invention

1. Identify large, accessible upper extremity peripheral vein; or the largest one visible or available or accessible
2. Fill a 50 mL or a 60 mL syringe with ozone (at 55 mcg/ml concentration on machine) at 5 mL past the 50 mL mark to 55 mL, or past the 60 mL mark to about 65 ml
3. A 27-gauge (infant scalp vein size) butterfly setup is attached to the syringe
4. A small amount of oxygen-ozone gaseous mixture is pushed out through the butterfly to flush it up to the 50 ml or 60 ml mark; say around 5-10 mL
5. A hook-and-loop tightening band is applied for best effect—simply a tourniquet does not work on everyone, and in patients on dialysis, sometimes even with prominent veins, a stick may not yield venous blood, even when the needle is in the vein. It is never a good idea to administer the gaseous mixture, if there is no flash of blood, as these veins blow-up and can be quite painful. In dialysis patients in whom huge ultrafiltration has been performed, it is important to utilize permacath, if they have one, to administer the oxygen-ozone gaseous mixture.
6. This is the protocol for using the permacath (also patented): First, wearing gloves, we wipe venous or arterial port with alcohol swab. Next, we unscrew port plug, and save within sterile wrapping of pre-loaded 5 mL saline syringe, to prevent contamination of that surface which will come directly in contact with the blood in the permacath. Thirdly, we aspirate heparin lock—around 3 mL (this will come along with some blood). Then, we lock the permacath with the permacath lock mechanism, between aspiration or infusion procedures, to avoid blood return and spillage. Afterwards, we flush with 5 mL sterile normal saline (pre-loaded syringe). Subsequently, we inject the above gaseous mixture of oxygen and ozone. Then, we flush again with 5 mL of sterile normal saline to empty the port of any gas. Then, we pack port with 3 mL sterile heparin at 1000 units-per-mL concentration. We wipe port plug with alcohol and screw back into position. Finally, before wrapping both ports with sterile gauze, we wipe both ports with alcohol swabs. We take care to swab heparin bottle with alcohol swab before and after injection of heparin; and to adhere to expiration dates on bottle (following opening of the bottle).

7. This ensures almost always, that the butterfly makes entry into the peripheral vein
8. Once the butterfly is within the vein, hook-and-loop tightening band can be released.
9. At around 1 mL per ½ to 1 minutes rate, the oxygen-ozone gaseous mixture maybe introduced into the vein, observing for local reactions, swelling, pain, infiltration. One might begin with 5 cubic centimeters (cc) first treatment for person 90 pounds (lbs.) or more in weight.
10. Treatment time is about 10 minutes for 20 cc. We push at the rate of about 1 cc every 0.5 to 1 minute—this may also be done utilizing a steady flow rate, intravenous (IV) infusion pump.
11. We can increase amount of gaseous mixture infused by around 5-10 cc each treatment unless the patient has a yeast or bacterial kill-off leading to flu-like symptoms—body aches, fever, joint pains and swelling, rash, which typically resolves in 1-2 days at the most (which has been called a very mild version of serum-sickness in the past), expresses discomfort, cough, chest tightness, facial flush, or vein irritation not helped by slowing infusion.
12. If there is pain, one must halt the treatment and resume much slower after ensuring that infiltration is not a problem.
13. For some reason, if it appears that the gaseous mixture does not flow easy into the vein, one might squeeze the arm above the butterfly with stroking movements proximally so that one might relieve "log jam" (accumulation of heavy O3 molecules) of gas.
14. For this reason, it is also better for the patient to keep all their limbs absolutely straight
15. One tries to retain 5 mL gaseous mixture, to flush at the end of the procedure, in order to discard the syringe as a sterile implement with a sterile needle.
16. Typically, the butterfly is utilized continuously, if there is a volume greater than 55 mL requiring to be infused. It has been our observation, that less is more in this therapy—that we can safely utilize just 20 mL of gaseous mixture per treatment (for reversal of chronic illnesses such as kidney, heart, diabetes and neurological), without any fears, to same effect as higher doses, except perhaps if going for the kill, as in AIDS, Hepatitis-C, and other such diseases. Typically, in chronic illnesses, a substantial, irreversible improvement in the disease, occurs by the 20th treatment.
17. We ensure patients have always eaten something before starting treatment, as we have rarely observed even diabetics who are on insulin (type I) become hypoglycemic (manifest symptoms of hypoglycemia—such as hunger and weakness or sweating, and when checked their sugar is under 100 mg/dl) during and after treatment—to the extent that we always keep energy and nutritional bars in the office to distribute to patients, if they've had nothing to eat before coming our way.
18. For safety sake, we also try not to exceed 50 mL of gaseous mixture until halfway through a course of 20 treatments—in fact, when it is exceeded, patient develops a strange and visible translucency under and around their eyeball—just above the facial maxillary ridge, and feels woozy, light-headed and dizzy for up to 2 hours' time—so this is a very important to note and follow.
19. One can always add more after a dozen treatments up to a total of around 110 mL—just remembering to clamp the butterfly tube, between syringe exchanges, in order to prevent air entry into the line (that is, clamp the butterfly tube, while exchanging the empty 50 mL syringe for the fully filled 60 mL syringe)
20. We try and observe patient for at least 10 minutes before the patient leaves (after making sure vein is pressed for 5 minutes, without bending arm). We take note of cough, chest tightness or anything unexpected. For the first treatment, it is better to observe patient for 30 minutes' time. If the patient has chest tightness or cough, encourage them to drink small sips of water, to take their minds off cough or chest tightness. Typically, this resolves within 30 minutes' time or so. The effect of the ozone molecules within the body (direct effect) is entirely gone within 45 minutes or so. Nothing adverse has ever come out of the chest tightness.
21. More peripheral veins require slower rate of gaseous mixture administration.
22. Some have reported that a feeling of weakness, numbness or altered sensation or loss of function or motor function, may begin on one side of the body within the first 30 minutes, which might last for several minutes (up to 30 minutes) after direct intravenous (DIV) and has not led to any residual effects (typically seen with several molecules of ozone adhering together, before they separate and get metabolized).
23. These side effects never happen with the first DIV (except cough or chest tightness), or during the actual treatment.
24. If the patient has experienced cough or chest tightness, we typically do not increase the dose until he/she has the same dose again without this sensation. Usually, this resolves within 1-2 treatments.
25. In the rare event that distressing chest symptoms occur (which can happen with in patients who've had destructive lung changes due to advanced AIDS or other illnesses), one may give oxygen at 0.5 to 3 liters per minute via nasal cannula to accelerate the resolution of the chest discomfort. The patient may not leave until they are well past the symptoms. We make them wait 5-10 minutes after the symptoms disappear (so that they are not perturbed when they leave or distressed) before they leave. They should be breathing O2 the entire time. No further addressing is typically required.
26. Warm compresses maybe given as needed for redness, pain and swelling, in the area of the vein, if it occurs post treatment, and, as a last resort, ibuprofen. To prevent this, we stress the importance repeatedly to patients, to ensure that they are taking Vitamin C to gut tolerance every 2 hours, 5-6 times a day (especially, on the actual day they receive the gaseous-mixture treatment, as the Vitamin C absorbs not only the free radicals that may be generated in excess by the treatment, but also, fortifies the vein wall by causing collagen deposition). Patients are also encouraged to drink up to 1 gallon of water everyday (particularly on the day they receive the treatment—if not contraindicated, as in CKD or ESRD or other conditions), and take live probiotic drink of several billion per ounce, at least 3 oz. daily or probiotic capsule containing at least several (5) billion cfu per capsule, to replace good gut bacteria, which are also killed by this treatment.
27. The above method also can be utilized to regenerate pancreas (or increase insulin sensitivity) in diabetics; it can also be utilized to regenerate neurons in stroke patients; to regenerate blood vessels in patients with coronary artery disease and carotid artery disease and any other peripheral arterial disease or vascular disease;

it can also be utilized for regenerating neurons in degenerative neurological illnesses; this method also can be utilized to regrow arteries and blood vessels in coronary artery disease and strengthen cardiac function in congestive heart failure and other cardiac diseases.

28. It is also to be noted, that this IV method is the absolutely best route of administration of the intravenous ozone-oxygen mixture—intravenously—and produces the greatest numbers of circulating stem and progenitors cells. However, the same effect can also be realized, through rectal administration, at a different concentration and utilizing different amounts; or taking some blood out (say around 200 mL) from the patient, mixing it with around 200 mL of the gaseous mixture (admixture method) and then putting it back intravenously, into patient; or dialyzing blood against the gaseous mixture (ozone dialysis), rather than dialysate (for an hour or so). In terms of the greatest effect on stem and progenitor cells the dialysis effect is the greatest of all routes of administration, followed by the IV route; and then the admixture modality followed by the rectal administration. Route matters to the extent of stem/progenitor release—this is important to know. Other methods may follow and are to be rated against these methods.

Supplemental Overview on the Invention

The invention is a process—the intravenous administration of a proprietary oxygen-ozone mixture, in a proprietary manner. A deficiency of the enzyme G-6PD is excluded by history of lack of allergy to Bactrim drug, or blood level (we have never observed a side-effect due to this, although it is recommended that this is tested). A machine which has been designed by a New York based company, to create this gaseous mixture with precision concentration controls (33 mcg/ml, 43 mcg/ml and 55 mcg/ml), and sterility, is employed in a specific manner, to create the gaseous mixture. This mixture is then injected in increasing doses starting with 10-20 mL, depending upon patient size and body habitus. At each session, 5 to 10 mL more can be given, up to a maximum of 110 mL. Within 20 sessions, kidney organ and other organs will regenerate, and their function will improve irreversibly. Some particular points on the invention to note:

This protocol also causes an increase in stem and progenitor cells in people over the age of fifty years, or by telomerase-based aging—greater than 50 years (biological age)—this protocol will eventually, it is predicted, be utilized in reversing aging and triggering healing of multiple chronic illnesses such as kidney failure, diabetes, heart disease and neurological diseases; by triggering HSC and HPC pluripotency; and in reversing acute radiation injury to hematopoietic stem and progenitor cells, potentially being a standard approach to treat injury caused by higher than normal doses of radiation.

It is also predicted that at some point, this protocol will be utilized or some version of it (such as a designer drug—chemical or polypeptide, which will identically mimic its effect on progenitor or stem cells), to obtain better HPC and HSC yields in autologous bone marrow transplantation, in older patients (age greater than 50), or patients requiring a second BMT for any kind of malignancy or benign condition—this use of the protocol is also being patented It is also predicted, that this procedure will increase the levels of telomerase—reversing aging And, this procedure increases the predisposition of HSCs and HPCs to de-differentiate/differentiate into their pluripotent versions, and repair any organ damage encountered—at any age—this is remarkable and being reported for the first time herein (beyond the age of 50)

It is also to be noted, that this (IV) is the absolutely best route of administration of the intravenous ozone-oxygen mixture—intravenously—and produces the greatest numbers of circulating stem and progenitors cells. However, the same effect can also be realized, through rectal administration, at a different concentration and utilizing different amounts; or taking some blood out (say around 200 mL) from the patient, mixing it with around 200 mL of the gaseous mixture (admixture method—utilizing manual or machine-based—what is known as major autohemotherapy under pressure, as by Herrmann or Zotzman) and then putting it back intravenously, into patient; or dialyzing blood against the gaseous mixture (ozone dialysis and described in this patent application for this purpose), rather than dialysate (for an hour or so). In terms of the greatest effect on stem and progenitor cells the dialysis effect is the greatest of all routes of administration, followed by the IV route; and then the admixture modality followed by the rectal administration. Route matters to the extent of stem/progenitor release—this is important to know. Other methods may follow and are to be rated against these methods.

Contraindications to the usage of this therapeutic mixture include—recent (less than 3 months) acute myocardial infarction, pregnancy, bleeding diathesis.

For the above protocol to be consistently effective, the following must be simultaneously or previously addressed (not every patient will need every element or all elements—but if our therapy does not work to stimulate appropriate increases in hematopoietic stem or other progenitor cell counts, one of these might be the cause—which is why it is recommended to address this beforehand). The present invention uses what is referred to as Fortifying Bodily Substrate, which are described in the following notations:

1. Vitamin D—5000 Units daily OR Vit D2 (not as preferred)—50,000 Units weekly (prescription) and follow up with checking levels every three months with your regular doctors—(To keep level around 50 ng/ml)—to facilitate return of neuronal syncytial transmission of above oxygen availability via intramural neurons, and other important survival messages, which might have waned with patchy neuronal death.

2. Vitamin B12 (preferably methylcobalamin or hydroxocobalamin—better) 1-3 mg IM (shot) every day for 10 days and then twice weekly for life. Essential for neuronal and adrenal gland function—essential—please don't follow blood levels—they are not an accurate representation of cellular availability—this facilitates neuronal health, nutrition, and return to viability, thereby pulling back into the network, marginal-health neurons—and additionally, helps cell process any and all ambient electromagnetic energy (a previously undescribed function of this vital vitamin, discovered by Dr. Yellapragada Subba Rao).

3. Mountain Rose Herbs' Curcumin Elixir (3 oz bottle for $30)—10 drops twice a day—increase to 30-40 drops four times daily as tolerated—remember turmeric is the most potent anti-inflammatory, anti-cancer, anti-infective agent on the planet; and it also predisposes to bleeding (something to be cautious of—if one accidentally cuts one's finger chopping something for example—please hold pressure for 10-15 minutes' time or until bleeding stops whichever is later, rather than the usually recommended 2-6 minutes' duration—normal bleeding time off anti-platelet agents). This facilitates the minimization of inflammation due to any cause—most potent anti-inflammatory agent, which must be administered in an absorbable format—to facilitate neuronal overall health, and long-term functionality, maintaining the neuronal circuitry. Particularly to be utilized if there is an acute flare of inflammatory underlying condition 4. All conditions which require steroid treatment, imply the body's intrinsic source of cortisol is not working in a healthy manner (the adrenal gland). It could point to adrenal fatigue, a disease of the 21st century, resulting from the drop in the number of functioning cortisol secreting cells in adrenal glands (and their neuronal stimulators and their shared common embryonal neuroendocrine precursors), which regular doctors fail to acknowledge—and can result in the loss or ill-health of all cells, particularly neurons, in the body from a lack of perfusion or adequate blood flow, or their death. Adequate rest (8 hours' of sleep); adequate hydration (half your weight in water ounces per day); adequate exercise; adequate Vitamin C (most important—take as much as 4-6 gm, every day of Emergen-C—rapidly dissolving powder Vitamin C—this will really help heal all injuries and skin); avoid caffeinated beverages—especially coffee; avoid eating late; snack regularly (every three hours or so and avoid heavy very widely interspersed meals); fresh green leafy vegetables; meditation (which I know you already do), yoga asanas and pranayama (which are of greatest significance and raise stem cell numbers); turning conscious mind off worries with humor, and so on . . . essential after a certain age. Adrenal fatigue contributes to neuronal and cellular disease and aging and demise first from a lack of perfusion, as in fact adrenal failure is in itself caused by the same.

5. Multivitamin and mineral nutrient tablet or Intramax (contains 400 essential nutrients and vitamins and is made in Plano, Tex.)—one capful in the morning (before 6 pm) everyday along with 8 oz of water at least—ideal to take this—this takes care of all unmet cellular and neuronal other nutritional needs.

6. Live probiotic—any one (curd or yoghurt or old rice water, or from pharmacy) or Zana BioJuices—3 oz every morning (best)—this also addresses inflammation very well by minimizing it, and replenishes microbial sources of nutrition, and assists in the removal of toxic intermediary products (cytokines and other inflammatory products) and waste products the body is too old to, or too diseased to handle, process and eliminate or recycle.

7. If something appears despite these preventive measures, one can use oxidative therapies or hyperbaric oxygen or both—as is described in the main body of the invention 8. Use of Rudraaksham beads, to negate any cause of chakra slowing down or failing to keep rotating—to facilitate absorption of ambient electromagnetic energy within the body (scientifically proven studies in the Eastern Medical literature)

9. Most Importantly, expanding Anaahatha Chakra—frog-like respirations at the solar plexus—with inhaling by expanding solar plexus actively (with hand on it to feel the expansion), and exhaling, by contracting lower abdomen from the lower border up—24 times each morning and evening—which facilitates proper lymphatic drainage, an essential component of health, nutrition, neuronal communication, and elimination of toxic substances and waste products from the body. The accordion like vacuum effect caused by this type of breathing, facilitates lymphatic drainage all over the body.

10. If there is a particular organ or organ system that is failing more than others or failed, a short course of exposure to Pule Electromagnetic Therapy of 77 Hz with 200 nanosecond frequency, can heal this back to a level equal to the rest of the body—this device is called EM Pulse (created by the brilliant and resourceful inventor Dr. Glen Gordon, whose licensed patented device we use), and maybe used on joints, kidneys, breast, heart and other accessible organs from a distance of 5 cm of penetration of these waves, which induce the over-expression of Heat Shock Protein 70 (as tested and reported by NASA), which facilitates the healing of any damage to a cell, short of reviving it from death.

Necessary Number of Treatments to Increase Stem and Progenitor Cells:

On average, in 1-2 treatments, the stem cell counts are observed to go up, as observed clinically, in the appearance of new veins, or increase in caliber of existing veins; also, the glomerular filtration rate (GFR) immediately improves and increases with the very first treatment (even in newly diagnosed ESRD patients, who might recover kidney function). Also, peripheral neuropathy, especially in uremia (uremic neuropathy), improves with the very first treatment. With this, balance, posture, proprioception in the feet, all improve. Also, hair turns back to original color from grey, wrinkles disappear, twinkles in patient's eyes reappear, youthful energy is back, hearing loss (due to aminoglycoside toxicity or aging) is recovered, vision improves, balance and co-ordination, speed of ambulation and sureness of step are increased. When GFR improves, in ESRD patients, they can regain renal function enough to reduce the number of times they need to take dialysis, or even recover entirely from needing dialysis. The only caveat to this is that the first time they undergo dialysis—the regained urine output from even just one treatment (from 100 mL brown dirty urine, to 800-1000 mL of yellow urine)—turns opaque white (which may be due to discharge of stem/progenitor cells formed during better oxygenation available to mitochondria—within kidney to repair kidney, or within kidney, to repair entire body—such as endothelial progenitors and others, which likely cause healing all over body), which only improves to cloudy urine, with several drops of oral turmeric a day (curcumin elixir)—which can prevent loss of newly generated stem cells/renal epithelial cells (as the case maybe) immediately, by shutting down the systemic significant inflammation associated with hemodialysis; followed by use of pulsed electromagnetic field therapy (PEMF) therapy, to keep stem cells within the kidney architecture, helping them differentiate faster and better, and adhere better faster—preventing loss of regenerated kidney tissue from stem and progenitor cells generated in-situ within the kidney or brought to the kidney by circulation, hemodialysis or any means of dialysis. Loss of fluid weight—even in typically elderly patients not known to have kidney failure suggests improvement in renal ultrafiltration. Better KT/V—from 1.07 to 1.32 to 1.48 to 1.58 to 1.6 at this time, without change in dialysis parameters or illness parameters—suggests improved what was previously known as "residual renal function"—but in this instance can only be accurately referred to as "regaining lost renal function due to renal regeneration"; increase in hemoglobin from 9.5 to 10.2, also without additional erythropoietin suggests the same thing as the previous point; interestingly, the ldl plummets—bring absorbed by the newly generated endothelium in the kidney and elsewhere, also suggesting that reversing renal failure or renal regenerative dysfunction—where it is known that, endothelial progenitor cells and hematopoietic stem cells are made from their immediate precursor cell known as hemangioblasts—vide benjamin dekel (not related to GFR or eGFR or RPF or any renal perfusion parameter), leads to improved whole body function; blood sugars are much better controlled; there is absolutely less fatigue; thought-process is clearer, patient is much more cheerful; energy levels come soaring back (increase in risk-taking activities—trips, gambling, new car purchase); increased speed of ambulation; in multiple sclerosis patients, we have witnessed increased limb strength and back strength, ability to sit straight in wheel chair, without slumping over; increased mental clarity; vastly improved mood, regaining of upper extremity functionality including signing name and pronation and supination and assisting lifting self from bed (none of which was possible for up to a decade before presentation); more rapid healing of fractures, and non-healing neuropathic foot wounds/ulcers/amputation/lymphedema due to chronic inflammation due to vascular hypo-perfusion or edema or anasarca.

Also, peripheral neuropathy, especially in uremia, improves with the very first treatment. With this, balance, posture, stability when walking fast, co-ordination, proprioception in the feet, all improve. Diarrhea resolves—of unknown origin.

On average, in 1-2 treatments, the stem cell counts are observed to go up, as observed clinically, in the literally sudden appearance of new veins, or increase in caliber of existing veins; the GFR immediately also improves and increases with the very first treatment (even in newly diagnosed ESRD patients, who might recover kidney function). Also, peripheral neuropathy, especially in uremia, improves with the very first treatment. With this, balance, posture, stability when walking fast, co-ordination, proprioception in the feet, all improve. Diarrhea of unknown origin also was observed to resolve.

In 3-4 treatments—More veins appear (except in CKD patients); gait stabilizes; proprioception returns; intellect and clarity of thought-process increases substantially (almost) exponentially; mood is vastly better. Twinkles in the eyes are back. There is a lot less fatigue—patients with chronic fatigue, don't sleep in the afternoons, for the first time in months. In patients with osteoarthritis, with the very first treatment, there is a reduction in pain; increase in mobility, which increases exponentially within the next few treatments; and overall there is an improvement in mood as well. Often, there is no need for a subsequent surgery for joint replacement or joint injections for symptomatic relief.

In 6-7 treatments, a jungle of veins appears, in previously poorly veined areas. Vision improves; ototoxicity due to aminoglycosides reverses. Faster gait; more intellectually efficient; more focus, concentration, more cheerful, more youthful. Interestingly, in some patients, there is a spike in risk-taking activity (gambling, new-car purchase), which are their underlying pre-existing character traits. Wrinkles resolve; hair color returns from gray.

In 20 treatments, irreversible organ and organ system improvements occur—from re-growing of muscle, in denervated areas, to re-growing nerves; regaining endurance for walking, core muscle strength, waving, handwriting (signatures), stamina, strength, core muscle strength, cognition, mood lifts and depression recedes, affect displays more emotion, spontaneous weight loss of 20 lbs. in patients who need to lose weight; regenerative renal pain—from regeneration of kidney—swelling and stretching of the capsule related to that. Early fracture healing is also observed by this method—in multiple sclerosis patients—and is being patented. There is less anasarca, lymphedema, vastly improved wound healing; vastly earlier fracture healing; significant increase in muscle mass in major muscle groups; increased stamina for activities; increases mental clarity; increased limb strength and core strength; increased endurance in physical therapy in amputees.

Subsequent to 20 therapies, is more maintenance therapy, and needs to be undertaken until improvement in creatinine clearance and improvement in serum creatinine and uremic markers (serum and urine metabolomics markers of CKD and uremia are likely to recover earlier, long before traditional poorly sensitive markers of renal dysfunction improve), is definitively and sustainably seen.

Also, studying changes in transcriptomics, proteomics and metabolomics (serum and urine), cellomics within Hemotopoietic Stem and Progenitor Cells, and Endothelial Progenitor Cells, and Nephron Progenitor Cells, and other progenitor and stem cells and precursor and effector cells (downstream proteomics and transcriptomics and cell changes—within and outside of mitochondria), are all protected by this patent (especially with those persons to whom this has been revealed by virtue of their being methods or other collaborators, or employees or other such associates).

Any drugs that may result from the study of the proteomics and transcriptomics and serum and urine metabolomics, and single-cell studies and changes in individual organs and organ-systems biology, and changes effected within individual cells, due to ozone-oxygen therapy given intravenously, is also covered by this patent, as it is the root patent.

Also, the effect of readily available oxygen on mitochondria, cellular respiration, and a study of transcription factors and other proteins being up-regulated and down-regulated systems biology effects of the improvements of cellular respiration, autophagy, apoptosis, aging, from cells all the way up to organism senescence everything in between included, are covered by this patent—which heralds a new field.

The interactions of new drugs—in development, chemicals, ligands, or (synthetic) polypeptides, with key elements (proteomics) of cellular changes caused by ready availability of oxygen (form this ozone-oxygen mixture), and presumably the several mechanisms of action and single main mechanism of action, resulting in the above changes is also being patented as they are being developed.

It is also hypothesized, based on a series of observations, that reversal of regenerative and excretory kidney failure utilizing any means, including the changes caused directly by the ozone-oxygen mixture, or any drug/ligand/substance/chemical/synthetic or naturally occurring, will result in human biological immortality. This is also being patented separately with more detail.

Based on our clinical observations with this gaseous mixture and its analogs, it can cause an increase in the circulation stem and progenitor and precursor cells, as described above, at any age, and allow for increased regenerative capacity or pluripotency potential of any of the above types of cells, to also manifest or return, at any age.

Additionally chemotherapy induced toxicity to bone marrow (leukemia patients who need bone marrow transplants and cannot mount the counts of stem cells needed for autologous transplants due to chemotherapy or aging—which is well documented in the literature) and other elements of the Regenerative Organ System; radiation induced toxicity to bone marrow and other elements of the Regenerative Organ System (by poisoning with radioactive isotopes or massive exposure or cosmic radiation exposure as for astronauts and aging); and any other cause, including aging induced bone marrow toxicity) whether cosmic radiation induced or metabolic pathways' changes induced), can be reversed by our above protocol, when implemented in full, utilizing all the steps.

Related Observations:
1. There appears to be a final common pathway of organismal demise
2. The mechanism for this appears to be patchy neuronal death
3. Anything that protects neurons, prolongs life and improves quality of life
4. Reversal of aging and disease, are related to the presence and numbers of circulating pluripotent stem cells, like Hematopoietic Stem/Progenitor Cells, making to the organ or organ system that is damaged, in good enough time, before chemotactic substances (acting as homing beacons), which cause stem cell/progenitor cell homing to site of injury, disappear, such as SDF-1, and their functionality which can be measured by the openness of chromatin network for promiscuous transcription of all sorts of functional transcription factor genes, as described in the classic Plenary paper in Blood Journal, 2002, by Koichi Akashi and Xi He.
5. Aging is due to consistent disappearance of every x neurons—for example every 5th neuron, progressing to the disappearance of every 2nd neuron; whereas disease is due to a concentrated disappearance of neurons within an organ or organ system (such as adrenal gland or pancreas or colon).
6. It is observed in all elderly patients, when they receive this protocol of regeneration with the hyper-availability of oxygen for oxidative phosphorylation, they void more number of times, even if they have no documented renal failure by creatinine clearance or calculated eGFR.
7. As described above, the kidney is first regenerated before veins, muscles, nerves, cartilage, and other organs or organ systems. The kidney is where the body first invests itself in regeneration, as evidenced by first an increase of GFR (even in patients for protracted periods on dialysis, who are typically incapable of performing significant uremic clearance unless first regenerated); and when that is followed by dialysis, a large number of regenerated kidney cells, are shed into urine (which have not yet, at this point—less than 48 hours, differentiated into adequately, or formed sufficient adhesion molecules to retain their place within the kidney)—until curcumin elixir was given; followed by PEMF, to make them adhere to where they need be and differentiate into what they need to differentiate into.
8. Once renal regeneration is secure, the rest of the body comes back—something which is suggested, based on these human observations and a previously conducted experiment on nephrectomized rats experiment, that even the smallest sliver of kidney tissue, if present, can function to regenerate the rest of the body (even if very little kidney tissue is present, rest of body can also regenerate, once the kidney function is adequate with ozone therapy (even though actual kidney tissue does not make a reappearance). In these rats, even though the traditional blood values of kidney excretory function, do not improve much with the initiation of regeneration, the longevity of the oxygen-treated-nephrectomized rats, with regard to control non-nephrectomized animals, is undiminished, suggesting that other biochemical parameters may be affected long before standard blood and urine excretory or eGFR function measuring tests are (such as metabolomics, and transcriptomics, and proteomics).
9. Therefore, we propose, that there is a fatal flaw in death (and not the death star) itself (in conjunction with our motto of Death to Death), which can be exploited or explored in a field of fields—namely, the regenerative organ system. What stimulates this Regenerative Organ System (including high quality time spent listening to the patient), what actions that we as physicians take that diminishes its functionality, such as administering different drugs (Stem and Progenitor Cell Counts and once they are sorted, their pluripotency can be assayed as described in the classic paper referenced, in Point 4 above).

Conclusory Statement:

The human body has a Regenerative (and recycling) Organ System—the grand overview of how the body is capable of infinite healing, as originally divined: the kidney is the "brain" of this system; the bone marrow is the "spinal cord" of this system; and the individual cellular members of this system are located in every organ and tissue, waiting to be activated or triggered.

These cells have been well described by the brilliant, original, talented, future Nobel winner, Dr. Arjun Raj of UPenn, and constitute immortal cells. How these cells communicate with each other and with the "brain" and "spinal cord" is mysterious—and will exceed previously described systems (paracrine, autocrine, endocrine, exocrine). We believe that it is Praanic (the substance of the spirit), or Electromagnetic (radiation within the body generated by cells), or both actually.

It is this regenerative organ system, that prevents the body from aging, acquiring any disease, and dying; and prevents the need for the inauguration and relentless (once initiated) execution of the "Final Common Pathway of Organismal Aging, Disease and Demise". For example, radio static being disease; and lowering radio volume being aging, turning off the radio being death, as metaphors for the flow of life energy within this extensively and deeply interconnected neuronal network. It is this pathway that we have been studying for 10 years now, at The Immortality Institute, located in Houston, Tex. Within this system, the kidney triggers new hematopoietic stem cell generation from hemangioblasts, which give rise to endothelial progenitor cells and hematopoietic stem cells. The kidneys also are known to secrete g-csf and erythropoietin, which stimulate the bone marrow in hematopoiesis.

This regenerative function of the kidney, does not depend upon actually its perfusion or eGFR. Indeed, only a sliver of kidney (with intact regenerative function), is required, to carry out the property of being the brain of the regenerative organ system. Also, this implies, that the signals being transmitted to the kidney, arise in the neurons in the blood vessel walls, where higher oxygen concentrations are sensed and transmitted syncytially, to vessels within the kidney, where the initiation of stem cell proliferation and release occur, rather than in the actual quantum of blood flow or supply, to the kidney.

Interestingly, we have demonstrated based on clinical observations, that we can probably induce greater numbers and pluripotency of hematopoietic stem cells, which are the one truly pluripotent stem cells, which already exist in the body (and are accessible via mobilization—including utilizing our protocol, in circulation in the elderly, and just like that, in the young), can travel all over the body within blood regenerating where they need to.

However, wherever there are still capillaries, be they lymphatic or vascular, there exists the possibility of transforming capillary endothelial cells, into hematopoietic stem cells, which can potentially regenerate the tissue as well. The analogy for this, is when the bricks of the road that is laid, turn into the construction workers, laying not only the highway, but also, the public utilities, lighting and nearby township, which they can only get to, by traversing the newly laid highway—an infinite, and gorgeously (one is sure) regulated loop the loop.

This endothelial hematopoietic transition (EHT) likely occurs under hypoxic (when blood supply is preferentially diverted elsewhere by the parasympathetic nervous system, during stress) conditions, but where neuronal signals still can reach. Obviously therefore, the inverse must also occur (Hematopoietic Endothelial Transformation). This, we are observing clinically, when utilizing our protocol.

EHT transition is perhaps limited by neuronal access (within capillary walls), to endothelial cells; neuronal access to endothelium, is enhanced by meditation, which redirects blood flow, to the luminal surface of all tubular structures within the body, by the parasympathetic nervous system, which is constantly active, with prolonged states of meditation.

The regenerative function of the kidney is lost when there is chronic stress. The recycling and regenerative function of the kidney, that is. When it stops recycling, it must excrete nitrogenous, what are now "wastes". That is when and where, its excretory function comes into a necessary play. This is also why, we have never been able to correctly predict, 100% of the time, unlike say, heart failure or liver failure, exactly what the functional status of the kidney—we are still devising exponential formulae, to calculate in every scenario of kidney failure, its correct function (that eGFR, which tallies exactly, with what it's measured gold standard filtration rate is).

To sum up, this is also why we must learn to reverse regenerative and excretory kidney failure and apply/offer it to all kidney failure patients and patients with chronic medical illness and other conditions such as myelo-ablation due to radiation toxicity or chemotherapy.

The incidence of chronic medical illness is the entire Medicare FFS population of 53 million people (each of whom has at least one chronic kidney disease and end stage renal disease, patients medical illness such as diabetes, heart failure, COPD, depression, stroke, kidney failure); 8 million or 14% of the above 53 million people, have 6 or more chronic medical conditions costing half of the annual expense on chronic medical illness, at least, and more (those who are covered by private insurers above and beyond Medicare). The cost of treating chronic medical illness, to Medicare ALONE is $1 trillion a year (and hypothetically, an equal amount, to private health insurers). Chronic kidney disease alone and end-stage renal disease together cost Medicare $100 billion a year, and private insurers, a lot more.

For when the recycling and regenerative function of the kidney is regained (a function that is lost, long before its excretory function is perhaps lost, resulting in worsening excretory failure of the kidney), all the body regenerates; and disease, aging and death, are banished.

Although the invention has been explained in relation to its preferred embodiment, it is to be understood that many other possible modifications and variations can be made without departing from the spirit and scope of the invention as hereinafter claimed.

What is claimed is:

1. A treatment method to increase circulation and pluripotency of stem and progenitor cells within a patient by a practitioner, the method comprises the steps of:
   (A) providing a medicinal-administration system including a syringe, an infusion device, and a tourniquet;
   (B) identifying an accessible peripheral vein on an upper extremity of the patient;
   (C) preparing a volumetric dosage of an oxygen-ozone mixture within the syringe of the medicinal-administration system;
   (D) applying the tourniquet to a cannulation area on the upper extremity and inserting the infusion device into the accessible peripheral vein of the patient before step (E);
   (E) transfusing the volumetric dosage of the oxygen-ozone mixture from the syringe, through the infusion device, and into the accessible peripheral vein of the patient at a specified rate by releasing the tourniquet from the cannulation area during step (E) after the practitioner witnesses a flash of blood within the cannulation area;
   (F) targeting a renal system and/or bone marrow of the patient with the volumetric dosage of the oxygen-ozone mixture to create stem and progenitor cells within the renal system and/or bone barrow of the patient; and
   (G) repeating steps (B) through (F) as a plurality of treatment sessions.

2. The treatment method to increase circulation and pluripotency of stem and progenitor cells of claim 1, wherein the infusion device is a 27-gauge butterfly setup and is in fluid communication with the syringe.

3. The treatment method to increase circulation and pluripotency of stem and progenitor cells of claim 1, further comprising the steps of:
   detecting an obstruction for transferring the volumetric dosage of the oxygen-ozone mixture during step (E); and
   stroking a proximal area on the upper extremity towards a heart of the patient in order to relieve the obstruction.

4. The treatment method to increase circulation and pluripotency of stem and progenitor cells of claim 1, wherein the specified rate is adjusted to be proportionately slower for a smaller diameter of the accessible peripheral vein.

5. The treatment method to increase circulation and pluripotency of stem and progenitor cells of claim 1, wherein the specified rate is approximately 1 mL per every 30 to 60 seconds.

6. The treatment method to increase circulation and pluripotency of stem and progenitor cells of claim 1, wherein the specified rate is reduced if the patient is experiencing pain or discomfort.

7. The treatment method to increase circulation and pluripotency of stem and progenitor cells of claim 1, wherein the patient is given oxygen through a nasal cannula if the patient is experiencing pain or discomfort.

8. The treatment method to increase circulation and pluripotency of stem and progenitor cells of claim 1, wherein the volumetric dosage of the oxygen-ozone mixture during an initial session is approximately within a range of 5 to 20 milliliters (mL) and proportionately depends upon a weight and a habitus of the patient, and wherein the initial session is from a one of the plurality of treatment sessions.

9. The treatment method to increase circulation and pluripotency of stem and progenitor cells of claim 1 further comprising the step of:
incrementally increasing the volumetric dosage of the oxygen-ozone mixture by a specified volume during each treatment session.

10. The treatment method to increase circulation and pluripotency of stem and progenitor cells of claim 9, wherein the specified volume is approximately within a range between 5 to 10 mL.

11. The treatment method to increase circulation and pluripotency of stem and progenitor cells of claim 9 further comprising the steps of:
providing twenty sessions within the plurality of treatment sessions;
preventing the volumetric dosage of the oxygen-ozone of a tenth session from exceeding approximately 50 mL, wherein the tenth session is from a one of the plurality of treatment sessions; and
preventing the volumetric dosage of the oxygen-ozone of a later session from exceeding approximately 110 mL, wherein the later session is from another one of the plurality of treatment sessions which occurs after the tenth session.

12. The treatment method to increase circulation and pluripotency of stem and progenitor cells of claim 1, wherein the volumetric dosage of the oxygen-ozone mixture is approximately 96% oxygen and 4% ozone.

13. The treatment method to increase circulation and pluripotency of stem and progenitor cells of claim 1, wherein appendages of the patient are held straight during step (E).

14. The treatment method to increase circulation and pluripotency of stem and progenitor cells of claim 1, wherein the patient is resting in a semi-recumbent position during step (E).

15. The treatment method to increase circulation and pluripotency of stem and progenitor cells of claim 1, wherein a plurality of dietary supplements is taken by the patient during the plurality of treatment sessions.

16. The treatment method to increase circulation and pluripotency of stem and progenitor cells of claim 15, wherein one of the plurality of dietary supplements is a daily dosage of Vitamin C.

17. The treatment method to increase circulation and pluripotency of stem and progenitor cells of claim 15, wherein one of the plurality of dietary supplements is a daily dosage of Vitamin D.

18. The treatment method to increase circulation and pluripotency of stem and progenitor cells of claim 15, wherein one of the plurality of dietary supplements is a daily dosage of Vitamin B12.

19. The treatment method to increase circulation and pluripotency of stem and progenitor cells of claim 15, wherein one of the plurality of dietary supplements is a daily dosage of curcumin.

20. The treatment method to increase circulation and pluripotency of stem and progenitor cells of claim 15, wherein one of the plurality of dietary supplements is a daily dosage of probiotic food and/or drink.

21. The treatment method to increase circulation and pluripotency of stem and progenitor cells of claim 15, wherein one of the plurality of dietary supplements is a daily dosage of water.

22. The treatment method to increase circulation and pluripotency of stem and progenitor cells of claim 1 further comprising the steps of:
providing a pulsed electromagnetic field therapy (PEMFT) device;
identifying a failing body part on the patient during the plurality of treatment sessions; and
applying an EM pulse at a specified frequency onto the failing body part with the PEMFT device.

23. The treatment method to increase circulation and pluripotency of stem and progenitor cells of claim 22, wherein the specified frequency is 77 Hertz (Hz).

* * * * *